United States Patent
Raymond et al.

(10) Patent No.: US 9,902,987 B2
(45) Date of Patent: Feb. 27, 2018

(54) METHOD FOR DETECTING AND DIRECTLY IDENTIFYING A MICROORGANISM IN A BIOLOGICAL SAMPLE BY AN OPTICAL ROUTE

(71) Applicant: BIOMERIEUX, Marcy l'Etoile (FR)

(72) Inventors: Jean-Claude Raymond, Bessenay (FR); David Mosticone, Sainte Consorce (FR); Antoine Vimont, Chaponost (FR); Florent Baril, Saint Foy les Lyon (FR); Jean-Pierre Flandrois, Lyons (FR); Thomas Junillon, Lyons (FR); Benoit Mallen, Tassin la Demi-Lune (FR)

(73) Assignee: BIOMERIEUX, Marcy l'Etoile (FR)

( * ) Notice: Subject to any disclaimer, the term of this patent is extended or adjusted under 35 U.S.C. 154(b) by 63 days.

(21) Appl. No.: 14/371,488

(22) PCT Filed: Jan. 9, 2013

(86) PCT No.: PCT/FR2013/050051
§ 371 (c)(1),
(2) Date: Jul. 10, 2014

(87) PCT Pub. No.: WO2013/104864
PCT Pub. Date: Jul. 18, 2013

(65) Prior Publication Data
US 2014/0349280 A1 Nov. 27, 2014

(30) Foreign Application Priority Data
Jan. 10, 2012 (FR) ..................................... 12 50249

(51) Int. Cl.
| | | |
|---|---|---|
| *C12Q 1/00* | (2006.01) |
| *C12Q 1/10* | (2006.01) |
| *C12C 1/00* | (2006.01) |
| *C12Q 1/04* | (2006.01) |
| *G01N 33/569* | (2006.01) |
| *G01N 33/543* | (2006.01) |
| *B01L 3/00* | (2006.01) |
| *C12M 1/34* | (2006.01) |

(52) U.S. Cl.
CPC .................. *C12Q 1/10* (2013.01); *C12C 1/00* (2013.01); *C12Q 1/04* (2013.01); *G01N 33/54326* (2013.01); *G01N 33/569* (2013.01); *B01L 3/5029* (2013.01); *C12M 41/36* (2013.01); *G01N 2333/255* (2013.01)

(58) Field of Classification Search
CPC ...... C12Q 1/10; C12Q 1/04; G01N 33/54326; G01N 33/569; G01N 2333/255; B01L 3/5029; C12M 41/36
See application file for complete search history.

(56) References Cited

U.S. PATENT DOCUMENTS

| | | | | |
|---|---|---|---|---|
| 5,843,699 | A * | 12/1998 | Strenkoski | ............... C12Q 1/04 435/16 |
| 7,351,548 | B2 * | 4/2008 | Rambach | ................. C12N 1/20 435/34 |
| 7,642,060 | B2 * | 1/2010 | Nagar | ...................... C12Q 1/04 435/4 |
| 2009/0081766 | A1 | 3/2009 | Fukushima et al. | |
| 2011/0020861 | A1 | 1/2011 | Colin et al. | |
| 2012/0165215 | A1 * | 6/2012 | Andersen | ............. C12Q 1/6837 506/9 |
| 2012/0329660 | A1 * | 12/2012 | Coull | ................... C12Q 1/6888 506/3 |

FOREIGN PATENT DOCUMENTS

| | | |
|---|---|---|
| EP | 0 446 972 A2 | 9/1991 |
| EP | 1 440 316 B1 | 12/2009 |
| FR | 2 928 656 A1 | 9/2009 |
| WO | WO 96/39533 A1 | 12/1996 |
| WO | WO 2007/106936 A1 | 9/2007 |
| WO | WO 2012/004540 A1 | 1/2012 |

OTHER PUBLICATIONS

Bangs Laboratories Inc. TechNote #201 Working with Microspheres, Beads Above the Rest, Aug. 29, 1999, pp. 1-16.*
Byrne et al., Antibody based Sensors: Principles, Problems and Potential for Detection of Pathogens and associated Toxins, Sensors, 2009, 9, pp. 4407-4445.*
Vimont et al., "Growth of Shiga-Toxin Producing *Escherichia coli* (STEC) and Bovine Feces Background Microflora in Various Enrichment Protocols," *Veterinary Microbiology*, 2007, vol. 123, pp. 274-281.
Kim et al., "Application of a Flow-Type Antibody Sensor to the Detection of *Escherichia coli* in Various Foods," *Biosensors & Bioelectronics*, 2003, vol. 18, pp. 1101-1107.
Yang et al., "Electrical/Electrochemical Impedance for Rapid Detection of Foodborne Pathogenic Bacteria," *Biotechnology Advances*, 2008, vol. 26, pp. 135-150.

(Continued)

*Primary Examiner* — Gary Counts
(74) *Attorney, Agent, or Firm* — Oliff PLC

(57) ABSTRACT

A method for detecting at least one microorganism present in a sample, that includes: a) in a first container, bringing the sample into contact with at least one culture medium, b) placing the first container in suitable conditions to permit growth of the microorganism or microorganisms, c) bringing some or all of the mixture being made of the sample and the culture medium into contact with a reaction mixture and a substrate for capturing the microorganism(s) in the first container or in a second container, the reaction mixture having a device for detecting the microorganism(s); d) detecting, within the first or second container, the presence of the microorganism or microorganisms detected by the detecting device and fixed on the capture substrate.

19 Claims, 2 Drawing Sheets

(56) References Cited

OTHER PUBLICATIONS

International Search Report issued in International Patent Application No. PCT/FR2013/050051 dated Feb. 25, 2013 (with translation).
Written Opinion issued in International Patent Application No. PCT/FR2013/050051 dated Feb. 25, 2013.

* cited by examiner

METHOD FOR DETECTING AND DIRECTLY IDENTIFYING A MICROORGANISM IN A BIOLOGICAL SAMPLE BY AN OPTICAL ROUTE

BACKGROUND

The present invention relates generally to the field of analysis, for example biological analysis. More specifically, the present invention relates to a method for detecting and directly identifying at least one microorganism by an optical route in an, optionally enriched, biological sample.

Microbiological analysis requires accurate methods, in which the time to obtain the result must be as short as possible.

In the medical field, it is necessary to predict and diagnose the risk of infection: the quicker and more accurate the diagnosis, the more effective the management of the patients, the risk of transmission being minimized. The approach is similar for animal health.

There are identical problems in the food industry. There, however, a distinction is made between:
 pathogenic microorganisms and their toxins, where research applies to the raw materials, intermediates, and marketed finished products,
 non-pathogenic microorganisms, used as indicators of quality of the production process, from the raw materials to the finished products, throughout the chain, and bacteria of technological interest such as ferments.

Rapid and precise detection of suspected contaminants makes it possible to control them and thus apply corrective measures.

Technically, microbiological analysis can employ one or more steps of pre-enrichment and/or enrichment, one or more steps of detection, and one or more steps of counting the microorganisms. For particular applications such as microbiological control in the food industry, a confirmation step may also be required, in order to comply with the standards in force in this field.

At present, no method exists for detecting a target microorganism in a large initial amount of sample, without employing an enrichment step.

The enrichment step employs selective or non-selective culture media, which aim to promote growth of the target microorganisms in biological or environmental samples, while limiting the growth of the non-target flora. The media are often used in containers of the sterile plastic bag type, in which they are brought into contact with the food samples or environmental samples, for purposes of resuspension and enrichment of the microorganisms being sought. This step is necessary in order to meet the requirement of detecting the potential initial presence of at least one target microorganism in an amount of sample that is very variable and optionally is very large, e.g. 25 grams (g) to 375 g diluted in 225 to 3375 milliliters (mL) in the culture medium. At the end of this enrichment step, an aliquot (from 5 microliters (µl) to 5 mL) is taken for carrying out the step of detecting the target microorganisms. Now, it is necessary for this aliquot to contain a sufficient amount of target microorganisms to ensure that they are systematically detected. A step of secondary enrichment or subculture may then be necessary.

The detection step is based historically on culturing the microorganisms on agar media, for detecting the metabolic characters of the microorganisms being sought. Conventionally, specific enzymatic substrates are used. These enzymatic substrates generally consist of two parts, a first part specific to the enzyme activity to be detected, also called the target part, and a second part acting as a marker, called the marker part, generally consisting of a chromophore or a fluorophore. Based on the choice of these substrates, depending on whether there is reaction or not, it is possible to characterize the nature of a microorganism or distinguish between different groups of microorganisms. Thus, appearance or disappearance of coloration or of fluorescence will be the signature of a genus or of a type of microorganism. In this respect, the use of chromogenic media allows simultaneous detection and identification of the microbes being sought. It simplifies the process and greatly reduces the time to obtain the result. We may mention, as a concrete example, the applicant's ChromID® media. These chromogenic media are based on detection of specific metabolic characters of the microbes being sought, for example beta-glucuronidase enzyme activity for *Escherichia coli*.

Immuno-assays constitute another of the technologies used for detection testing. They make use of the immunogenic characteristics of the microorganisms being sought. Non-exhaustively, we may mention the techniques of immunofluorescence, the ELISA (Enzyme-Linked ImmunoSorbent Assay) techniques, competitive or of the sandwich type. These techniques employ a step of so-called indirect detection that employs a secondary antibody conjugated with an enzyme for subsequent detection via a substrate specific to the latter.

Document EP-B-1 440 316 describes for example a device for detecting microorganisms. This device consists of a solid substrate, on which capture partners specific to the target microorganisms, such as antibodies, are fixed. The capture substrate is then placed in various containers comprising the sample to be analysed and the various reagents for carrying out an ELISA reaction.

This step of so-called indirect detection then involves (following the enrichment step) the execution of various treatment steps (taking the sample, heating, centrifugation, washing, etc.) of the sample before the screening/detection step, which consequently make the operating protocol more complex, make the analysis less convenient and increase the time to supply the results.

Finally, the techniques of molecular biology, based on the genomic characters of the microorganisms being sought, are also employed for detecting and identifying the target microorganisms. We may mention, as examples, the conventional techniques of amplification such as PCR (Polymerase Chain Reaction) and NASBA (Nucleic Acid Sequence Based Amplification), which can be coupled to techniques for real-time detection known by a person skilled in the art. Nevertheless, these techniques require an arduous step of preparation of the samples, consisting of isolating the microorganisms, lysing them in order to release the nucleic acids, and finally purifying the latter. This also has a direct effect on the complexity of the operating protocol, making the analysis less convenient and increasing the time to supply the results.

Regarding the confirmation step, it is more particularly associated with microbiological analysis in the food industry. In fact, when the result of the methods developed previously is positive, it is necessary to confirm the presence of the pathogen being sought. This requires an additional test and the use of a principle of detection different from that used in the first analysis. The techniques described above are used at leisure for confirmation.

The complete and accurate identification of a microorganism in a sample therefore requires several successive steps: enrichment, optionally subculture, detection and confirmation. Standardization of the tests used routinely has allowed automation of the methods of detection, but they still take a long time. A drawback of the prior art is in fact that these steps are carried out sequentially and require a large number of time-consuming manipulations, thus having an impact on the time taken to supply the results.

SUMMARY

In view of the technical problems raised by the prior art considered above, one of the essential aims of the present invention is to provide a simplified method for the detection, identification and confirmation of the microorganisms present in samples, especially food samples.

Another aim of the present invention is to provide a method for detecting and identifying the microorganisms, which makes it possible to reduce the necessary time and cost for analysis of the sample.

These aims, among others, are achieved by the present invention, which relates firstly to a method for detecting at least one microorganism, said method essentially comprising the following steps:
   a) in a first container, bringing said sample into contact with at least one culture medium,
   b) placing said first container in suitable conditions to permit growth of the microorganism or microorganisms,
   c) bringing some or all of the mixture consisting of the sample and the culture medium into contact with a reaction mixture and a substrate for capturing said microorganism(s) in said first container or in a second container, said reaction mixture comprising means for detecting said microorganism(s);
   d) detecting, within said first or second container, the presence of the microorganism or microorganisms detected by the detecting means and fixed on the capture substrate.

According to a particular embodiment, the method according to the invention comprises an intermediate step c') consisting of placing the first or second container in suitable conditions to permit growth of the microorganism or microorganisms.

According to another particular embodiment, the method according to the invention comprises an additional step e) consisting of confirming detection of the microorganism or microorganisms detected. Preferably, the confirmation step e) is carried out using a detecting means identical to or different from the detecting means used for detection.

Advantageously, at least one specific or non-specific binding partner of the microorganism or microorganisms is fixed on the capture substrate. According to a preferred embodiment of the invention, the specific binding partner is taken from the group comprising: antibodies, Fab fragments, Fab' fragments, aptamers, recombinant or non-recombinant phage proteins, phages or any other ligand well known by a person skilled in the art.

The capture substrate can be any suitable substrate allowing detection of the microorganisms. We may notably mention particulate substrates, optionally magnetic, or single-piece substrates, optionally porous. It can be quite simply an inert substrate, such as a plate made of plastic or glass fibre. The capture substrate can advantageously be sensitized with a binding partner, optionally specific. The capture substrate can also be a compressible single-piece substrate.

Advantageously, the substrate can be protected by a protective film.

According to another particular embodiment, it is possible to execute detection and confirmation with the same technology.

Preferably, detection of the microorganism or microorganisms is carried out in real time. However, as an alternative, detection of the microorganism or microorganisms can be carried out, at the end point, at the end of a step of growth of said microorganism(s).

According to a particular embodiment of the method according to the invention, the first and/or the second container is a homogenizing bag. They can also be rigid containers such as flasks, bottles or tablet containers.

According to another particular embodiment of the method according to the invention, the detection step can be carried out using a reader. Such a reader can consist for example of a camera pointing at the capture substrate, for recording or analysis of images of said support.

BRIEF DESCRIPTION OF THE DRAWINGS

The aims and advantages of the present invention will be better understood in light of the detailed description given below, in conjunction with the drawings, where.

DETAILED DESCRIPTION OF EMBODIMENTS

Figure 1:
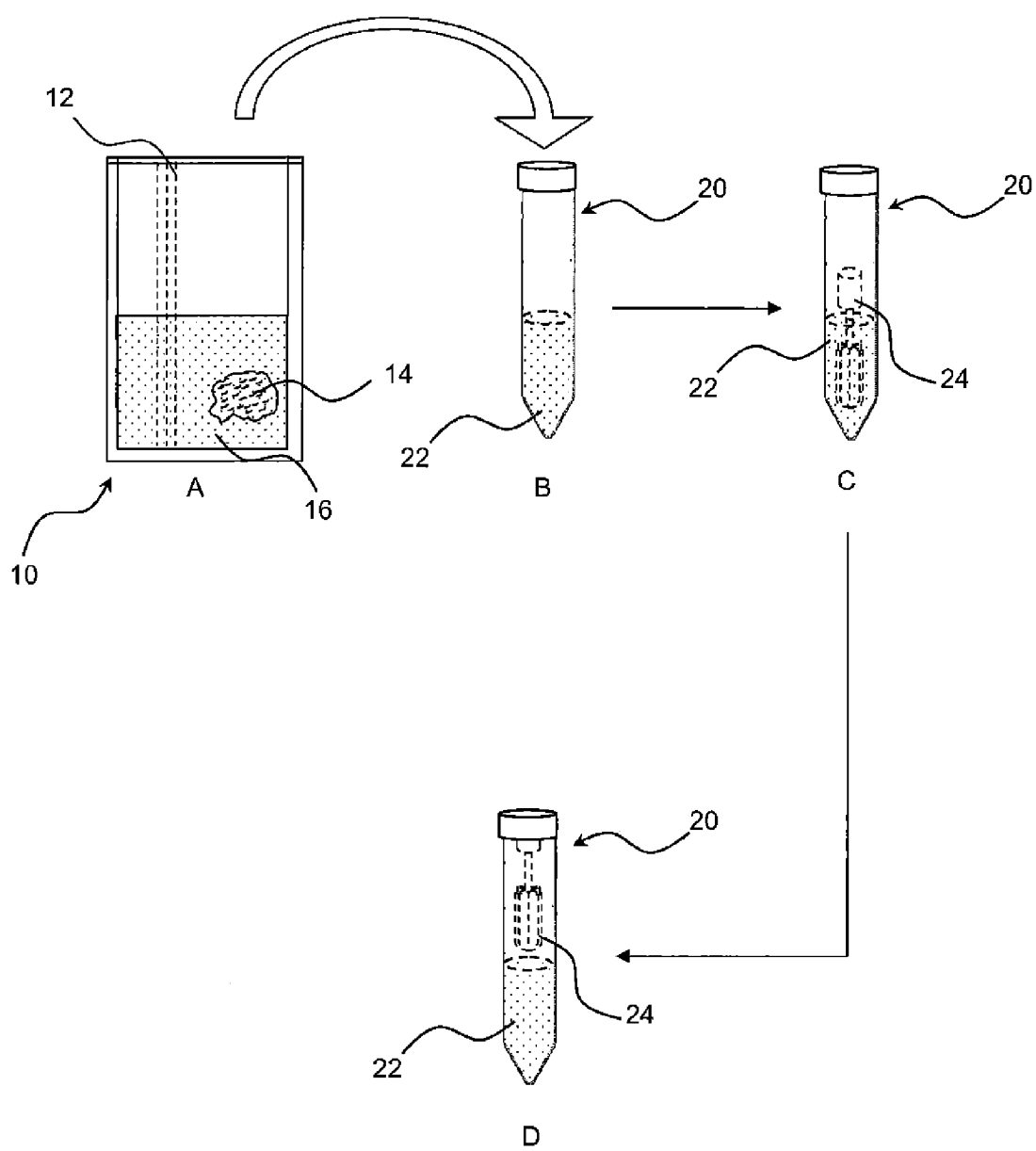
FIG. 1 is a schematic representation of the different steps of the method according to a first embodiment of the invention.

According to a first embodiment of the present invention, the method for detecting or for identifying microorganism(s) consists of employing a sterile plastic homogenizing bag, conventionally called Stomacher® bag. Such a bag is referenced 10 in FIG. 1A. This bag 10 consists of two roughly rectangular sheets of plastic, joined together on three sides, so as to define an internal space intended to receive the culture medium and the sample to be analysed. It additionally comprises a filter 12 of roughly rectangular shape, joined to the sheets on one side, separating the internal space into two.

During step A, the closed homogenizing bag 10 is incubated with a food sample 14, consisting in this case of a sample of unpasteurized milk cheese. This food sample 14 is immersed in an enrichment medium 16, which can be selective or non-selective. Incubation can be carried out at temperatures between 25 and 44° C. for 6 to 48 h.

A fraction of the enrichment medium is then taken in the homogenizing bag 10 and transferred during step B to a secondary container, consisting here of a tube 20. This tube 20 comprises a reaction mixture 22. Said reaction mixture 22 can consist of a diluent (e.g. tryptone salt broth) suitable for maintaining integrity of the target microorganisms, and at least one detecting means. The detecting means can be a dye that is able to stain the microorganisms present in the fraction of enrichment medium transferred, obtained from the food sample 14. The detecting means can also be a fluorescent compound that makes the microorganisms fluorescent. When we wish to perform a subculture in tube 20, the reaction mixture can contain, in addition to the nutrients, a selective system allowing the population of target bacteria to increase.

According to a particular example, the detecting means is based on the reduction of triphenyl 2-3-5-tetrazolium chloride (TTC) by the microorganisms. Simultaneously with growth of the microorganisms, TTC (colourless in its non-reduced form) is internalized by said microorganisms, and then reduced within the cytoplasm by the latter to triphenylformazan (red), thus staining said microorganisms red so that they can then be detected on the substrate. Other tetrazolium salts can be used (CTC, MTT, etc.). Moreover, compounds for speeding up the reaction of reduction of the tetrazolium salts can be added to the reaction mixture.

It is also conceivable to use membrane stains, such as gentian violet or fuchsin.

In the case when the detecting means is a fluorescent compound, it can be acridine orange or fluorescein diacetate.

Figure 2:
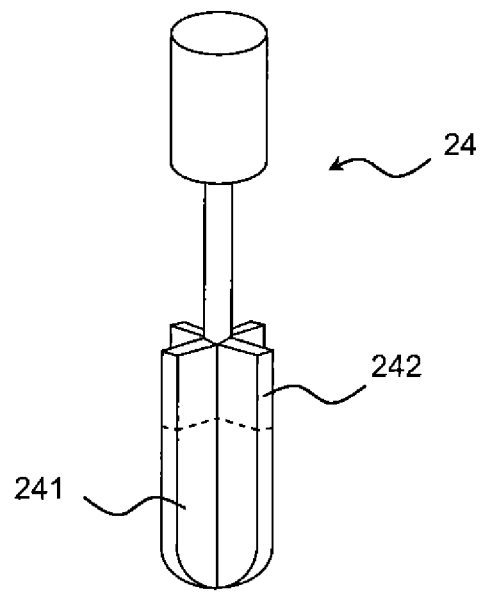
FIG. 2 is a schematic representation of a sensitized capture substrate.

In step C, a sensitized capture substrate 24 is put in tube 20 and is kept immersed in the reaction mixture 22 by any suitable means. The sensitized capture substrate 24 is functionalized with at least one specific binding partner of a target microorganism to be detected. The capture substrate can consist of any substrate suitable for fixation of specific binding partners and well known by a person skilled in the art. As a non-limiting example, a suitable capture substrate can be made of irradiated polystyrene, such as that marketed by the company Nunc/Thermo Scientific (Cat. No. 472230). A capture substrate of this kind is shown schematically in FIG. 2, with the reference 24. According to a preferred embodiment, the lower portion can advantageously be divided into two. The zone referenced 241 can be sensitized with a solution of binding partners (polyclonal antibodies, monoclonal antibodies, Fab' or Fab'2 fragments, aptamers, phage proteins), whereas the upper portion 242 remains free from any binding partner and thus plays a role of negative control. The techniques for sensitizing substrates with specific binding partners are well known by a person skilled in the art.

According to one alternative of the method according to the invention, it may be advantageous to carry out a step of subculture, once the capture substrate 24 is immersed in the reaction mixture 22. This subculture consists of incubating tube 20 for 1 to 18 h, at temperatures between 25 and 44° C. According to this alternative, the intensity of staining of the microorganisms increases simultaneously with their growth owing to the detecting means contained in the reaction mixture. Analysis can then be carried out in real time.

Figure 3:
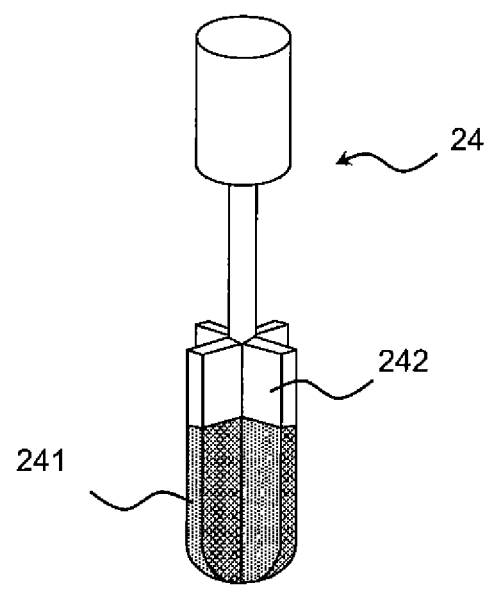
FIG. 3 is a schematic representation of the sensitized capture substrate shown in FIG. 2, after analysis with a positive result.

Once there is effective capture of a certain amount of stained or fluorescent target microorganisms (in the case of a positive sample), there is a change in the optical properties of the substrate through appearance of coloration or fluorescence on the latter (i.e. transduction of the biological signal). This coloration or fluorescence of the capture substrate is then detectable by eye or can be measured using an automatic reader such as a camera. The capture substrate is shown schematically in FIG. 3, after analysis with a positive result. As can be seen, zone 241 appears coloured owing to fixation of the target microorganisms on the specific binding partners. For its part, zone 242, performing the role of negative control, still has the initial colour of the capture substrate.

To facilitate reading, the sensitized capture substrate should preferably no longer be in contact with the reaction mixture. For this purpose, it can be envisaged for example to remove the capture substrate 24 from said reaction mixture by any suitable means, as is clearly shown in step D, in FIG. 1. As explained above, the reading can be taken at the end point, as dotted lines or in real time.

According to another alternative of the method according to the invention, the capture substrate consists of sensitized particles, namely bearing a specific or non-specific binding partner of the microorganism or microorganisms to be detected. Detection is then preferably indicated by appearance of a coloration or fluorescence of the initially colourless sensitized particles, due to binding of the target microorganisms to the latter, during the reaction.

According to a particular embodiment, the sensitized particles can be magnetic particles. Reading can then be done manually and visually, using a magnetizing system that will allow collection of the magnetic particles on which the stained or fluorescent microorganisms are captured, in the form of clusters against the container wall. Movement of the magnetizing system vertically upwards makes it possible to remove the cluster of magnetic particles from the reaction mixture and thus facilitate analysis. It can also be envisaged to immerse the magnetizing system directly in the container, in order to collect the magnetic particles on which the microorganisms are fixed. In this case the magnetic particles will become fixed directly on the magnetizing system, which then becomes coloured or fluorescent.

According to another embodiment of the method according to the invention, the reaction mixture and the capture substrate, as described above, are added directly to the first container at the end of the enrichment step. The detection step is therefore carried out in said first container without transferring some or all of the mixture consisting of the culture medium and the sample to be analysed to a second container. Prior to this detection step, a subculture can optionally be carried out in order to increase the population of target microorganisms.

It should be noted that, advantageously, the capture substrate can be protected using a protective film. The purpose of this film is to prevent fouling of the capture substrate. In fact, such fouling is likely to impair the capture performance of said substrate. Such a film can be placed permanently on the capture substrate. Alternatively, it can be a film that can dissolve after a certain time of contact with the liquid culture medium.

The method according to the invention is particularly advantageous because at the end of the analysis, only the containers identified as positive by the detecting system (described below) are opened in order to carry out additional analyses for confirming the presumptive result obtained. The confirmation step can be carried out by means of technology different from that employed in the method according to the invention.

The aim of the examples presented below is to present different embodiments of the method according to the invention and the results obtained. They do not limit the invention in any way.

EXAMPLES

Example 1: Optical Detection of *Salmonella* Napoli, by Means of a Sensitized Substrate, in a Food Sample in Subculture in a Reaction Mixture The aim of this experiment is direct detection of the presence of the target bacterium *Salmonella* Napoli in a food sample in subculture in a reaction mixture, by means of a sensitized substrate made of irradiated polystyrene, marketed by the company Nunc/Thermo Scientific (Cat. No. 472230) and shown in FIGS. 2 and 3.

As detailed below, detection is performed during the reaction step by immersing the capture substrate sensitized with a recombinant phage protein specific to *Salmonella* in a tube that contains the enriched sample, diluted to 1/100th in the reaction mixture.

Protocol:

Step 1: Resuspending the Samples in the Primary Enrichment Medium

Two samples are prepared as follows:

Sample A: In a homogenizing bag, 25 g of unpasteurized milk cheese contaminated with 5 colony forming units (CFU) of *Salmonella* Napoli is resuspended in 225 mL of Buffered Peptone Water (BPW) (bioMérieux, Ref. 42043), supplemented with 1 ml of Supplement SPT (bioMérieux, Ref. 42650);

Sample B: In a homogenizing bag, 25 g of unpasteurized milk cheese not contaminated with *Salmonella* Napoli is resuspended in 225 mL of BPW (bioMérieux, Ref. 42043) supplemented with 1 mL of Supplement SPT (bioMérieux, Ref. 42650).

Step 2: After 16 h of Incubation, Transfer of a 0.1-mL Aliquot from the Homogenizing Bag to the Reaction Tube 0.1 mL from the Sample A homogenizing bag is transferred to the reaction tube containing 10 mL of SX2 (bioMérieux, Ref. 42121) and 1.6 g/L of TTC (bioMérieux, Cat. No. 04568088). This gives Sample A'.

A similar operation is carried out for Sample B.

Step 3: Immersion of the Sensitized Substrates in the Reaction Tubes Before Subculture and Reaction The sensitized capture substrate is placed in each tube (Samples N and B'). The tubes are then closed again and incubated in a stove at 37° C. for 6 h.

Step 4: Reading the Capture Substrates at the End of the Incubation Period

At the end of incubation (6 h at 37° C.) and following non-specific reduction of TTC by all of the bacteria present in the sample (i.e. belonging to the additional flora and the target flora), the reaction mixture has turned red. Thus, in order to observe the capture substrate, revealing whether the sample analysed is positive or negative, the tubes are slanted so as to isolate said capture substrate from the reaction mixture.

In accordance with the experimental design, the capture substrate placed in sample A' appears coloured red, confirming that sample A' is positive, whereas the capture substrate placed in sample B' remains colourless, confirming that sample B' is negative. Analysis of these same samples by the VIDAS® SPT method, marketed by the applicant (ref. 30707), led to similar results, thus confirming the results obtained by optical reading of the sensitized capture substrate.

Example 2: Optical Detection of *Salmonella* Napoli in an Enriched Biological Sample, by Means of a Sensitized Substrate Immersed in a Reaction Mixture The aim of this experiment is direct detection of the presence of the target bacterium *Salmonella* Napoli in an enriched food sample, by means of a sensitized substrate made of irradiated polystyrene, marketed by the company Nunc/Thermo Scientific (Cat. No. 472230) and shown in FIGS. 2 and 3.

As detailed below, detection is performed during the reaction step by immersing the sensitized capture substrate with an anti-*Salmonella* recombinant phage protein in a tube containing the enriched sample, diluted to 1/2 in the reaction mixture.

Protocol:

Step 1: Resuspending the Samples in the Primary Enrichment Medium

Two samples are prepared as follows:

Sample A: In a homogenizing bag, 25 g of minced steak contaminated with *Salmonella* Napoli is resuspended in 225 mL of BPW (bioMérieux, Ref. 42043) supplemented with 1 mL of Supplement SPT (bioMérieux, Ref. 42650);

Sample B: In a homogenizing bag, 25 g of minced steak not contaminated with *Salmonella* Napoli is resuspended in 225 mL of BPW (bioMérieux, Ref. 42043) supplemented with 1 mL of Supplement SPT (bioMérieux, Ref. 42650);

Step 2: After 16 h of Incubation, Transfer of a 1-mL Aliquot from the Homogenizing Bag to the Reaction Tube 1 mL from the Sample A homogenizing bag is transferred to the reaction tube containing 1 mL of tryptone salt (bioMérieux, Ref. 42076) supplemented with 10 of gentian violet (bioMérieux, Ref 55545). This gives Sample A'.

A similar operation is carried out for Sample B.

Step 3: Immersion of the Sensitized Substrates in the Reaction Tubes Before Reaction The sensitized capture substrate is placed in each tube (Samples A' and B'), as described below. The tubes are then closed again during the reaction period.

Step 4: Reading the Capture Substrates at the End of the Reaction Period

At the end of the reaction (40 min at room temperature), all of the bacteria present in the sample (i.e. belonging to the additional flora and the target flora) are stained violet. Thus, in order to be able to observe the capture substrate, revealing whether the sample analysed is positive or negative, the tubes are slanted so as to isolate said capture substrate from the reaction mixture.

In accordance with the experimental design, the capture substrate placed in sample A' appears coloured violet, confirming that sample A' is positive, whereas the capture substrate placed in sample B' remains colourless, confirming that sample B' is negative. Analysis of these same samples by the VIDAS® SPT method, marketed by the applicant (ref. 30707), led to similar results, thus confirming the results obtained by reading the sensitized capture substrate by eye.

The invention claimed is:

1. A method for detecting a target microorganism present in a sample, the method comprising:
   incubating, in a homogenizing bag, a sample mixture containing the sample and a culture medium for 6 to 48 hours to permit growth of the target microorganism;
   transferring at least a fraction of the incubated sample mixture from the homogenizing bag to a secondary container that contains a reaction mixture to detect microorganisms in the combined reaction mixture and incubated sample mixture, the reaction mixture comprising a dye, membrane stain, or a fluorescent compound, that colors or causes to fluoresce the microorganisms present in the combined reaction mixture and incubated sample mixture;
   immersing, in the combined reaction mixture and incubated sample mixture, a substrate configured to specifically capture the target microorganism; and
   monitoring for an appearance of coloration or fluorescence of the capture substrate, wherein coloration or fluorescence of the capture substrate indicates that the target microorganism is fixed on the capture substrate.

2. The method according to claim 1, further comprising:
   incubating the capture substrate in the combined reaction mixture and incubated sample mixture in suitable conditions to permit growth of the target microorganism before monitoring for the appearance of coloration or fluorescence of the capture substrate.

3. The method according to claim 1, further comprising: confirming detection of the target microorganism after the monitoring.

4. The method according to claim 1, wherein at least one specific binding partner of the target microorganism is fixed on the capture substrate.

5. The method of detection according to claim 4, wherein the specific binding partner is selected from the group consisting of antibodies, Fab fragments, Fab' fragments, aptamers, recombinant or non-recombinant phage proteins, and phages.

6. The method according to claim 1, wherein the monitoring is carried out in real time.

7. The method of detection according to claim 1, wherein the secondary container is a flask, a bottle, a tablet container, or a tube.

8. The method according to claim 1, wherein the capture substrate is a single-piece or particulate substrate, optionally porous.

9. The method according to claim 8, wherein the capture substrate is protected by a protective film.

10. The method according to claim 8, wherein the capture substrate is a particulate substrate of sensitized particles.

11. The method according to claim 10, wherein the sensitized particles are magnetic.

12. The method according to claim 8, wherein the capture substrate is a compressible single-piece substrate.

13. A method for detecting a target microorganism present in a sample, the method comprising:
    incubating, in a homogenizing bag, a sample mixture containing the sample and a culture medium for 6 to 48 hours to permit growth of the target microorganism;
    removing a fraction of the incubated sample mixture from the homogenizing bag;
    introducing the fraction of the incubated sample mixture to an unconnected secondary container that contains a reaction mixture that colors or causes to fluoresce microorganisms present in the combined reaction mixture and incubated sample mixture, the reaction mixture comprising a dye, membrane stain, or a fluorescent compound;
    monitoring for a first appearance of coloration or fluorescence from the microorganisms in the combined reaction mixture and incubated sample mixture; and
    when the first appearance of coloration or fluorescence is detected, immersing, in the combined reaction mixture and incubated sample mixture, a substrate configured to specifically capture the target microorganism, and monitoring for a second appearance of coloration or fluorescence from the microorganisms on the capture substrate, wherein the second appearance of coloration or fluorescence indicates that the target microorganism is fixed on the capture substrate.

14. The method of detection according to claim 13, wherein the secondary container is a flask, a bottle, a tablet container, or a tube.

15. The method according to claim 13, wherein the capture substrate is a single-piece or particulate substrate, optionally porous.

16. The method according to claim 15, wherein the capture substrate is protected by a protective film.

17. The method according to claim 15, wherein the capture substrate is a particulate substrate of sensitized particles.

18. The method according to claim 17, wherein the sensitized particles are magnetic.

19. The method according to claim 15, wherein the capture substrate is a compressible single-piece substrate.

* * * * *